United States Patent [19]

Mittelmeier et al.

[11] Patent Number: 4,654,464
[45] Date of Patent: Mar. 31, 1987

[54] BONE SUBSTITUTE MATERIAL ON THE BASE OF NATURAL BONES

[75] Inventors: Heinz Mittelmeier, Homburg-Schwarzenbach; Bernhard Mittelmeier, Zweibrücken; Beat Leu, Hergiswil, all of Fed. Rep. of Germany

[73] Assignee: Oscobal AG, Selzach, Switzerland

[21] Appl. No.: 662,189

[22] Filed: Oct. 18, 1984

[30] Foreign Application Priority Data

Oct. 20, 1984 [EP] 10201984 .................. 83810483

[51] Int. Cl.$^4$ ............................................. A61F 1/00
[52] U.S. Cl. ................................. 623/16; 128/92 C; 128/92 G
[58] Field of Search .............. 623/16; 128/92 C, 92 G

[56] References Cited

U.S. PATENT DOCUMENTS 4,314,380 2/1982 Miyata et al. ...................... 623/16

FOREIGN PATENT DOCUMENTS

| | | |
|---|---|---|
| 0012959 | 7/1980 | European Pat. Off. . |
| 0058867 | 9/1982 | European Pat. Off. . |
| 961654 | 4/1957 | Fed. Rep. of Germany . |
| 2717506 | 5/1978 | Fed. Rep. of Germany . |
| 2840064 | 3/1980 | Fed. Rep. of Germany . |
| 3038047 | 4/1981 | Fed. Rep. of Germany . |
| 2078696 | 1/1982 | United Kingdom . |

Primary Examiner—John Kight
Assistant Examiner—M. L. Moore
Attorney, Agent, or Firm—Marks Murase & White

[57] ABSTRACT

The bone substitute material on the base of natural bone is rendered completely free of albumin and antigen by premaceration, pyrolization and sintering and its frame work consists of only the natural mineral structure of the natural bone.

In the process of production of this bone substitute material the bone pieces are submitted to a pretreatment with warm water for removing of the soft parts, subsequently takes place a dealbumination by means of a solution of 10 to 30% $H_2O_2$ in a shaking machine and a degreasing with ether. The bone pieces treated in this way are subsequently submitted to a combustion in a stove at 400° C. to 1500° C. and then to a sintering.

This bone substitute material which may exist in the shape of the bone part to be replaced forms a form stable matrix for the bone regeneration in which only pure "mineral bone" is present so that no immunogen reactions can take place. The process which includes combustion and sintering is considerably shorter than known processes.

19 Claims, No Drawings

4,654,464

BONE SUBSTITUTE MATERIAL ON THE BASE OF NATURAL BONES

BACKGROUND OF THE INVENTION

The present invention relates to a bone substitute material on the base of natural bones and to a process of production thereof whereby the bones pieces are submitted to a pretreatment for removing the soft parts then to a dealbumination by means of a solution of at least 10% $H_2O_2$ or a solution of trypsin and then to a treatment by means of ether. Such a bone substitute material and such a process for the preparation of adequate bone capable of reproduction is described in DE-A-961 654 and known under the name of "Kieler Knochenspan". This heteroplastic bone substitute material is obtained from calves and young bovine in which soluble proteins, grease and humidity are removed by special chemical processes so that finally only the network of the bone remains which is comprised of the collagen base substance of the bone and the mineral component of the bone material. This bone substitute material could not fulfill the expectations required for the orthopedic-surgical practice and extensive histological investigations have shown that although at the surface of this bone substitute material a bone deposit partially occurs the latter is obviously hindered by certain foreign body reactions which are due to the still remaining foreign collagen.

In the last two centuries the use of endoprothetics employing alloplastic for the body compatible foreign material and made from metals, plastics and bone cement has strongly increased due to the fact that relatively rapid and good results in the domain of articulation can be achieved which could not be achieved by transplantations of bone parts of natural origin. However, these technical products of substitution are also subjected to wear during use, involve considerable anchoring problems and are not capable of natural regeneration, all of which limits their field. This is particularly true in the domain of the diaphysis where prothetic bridges have not proved successful so that they only serve if necessary as palliative measures for patients with malignant bone tumors and a short life expectation.

The ideal function of a bone substitute is always, when possible, to give rise to regeneration with natural, vital, adaptable bone structures, more particularly for young people having a long life expectation. This purpose cannot be fulfilled with the endoprothetic, however valuable its possibilities are.

In the last two years artisians have tended to produce bone substitute material from synthetic calcium phosphates or hydroxylapatite. This material has the advantage of form stability and so may serve as a matrix for the regeneration of bone. However this matrix cannot be loaded very much. In cases of cross-sectional bone defects it is therefore necessary to execute an additional supporting osteosynthese, normally by means of a metallic plate bridging the remaining blunt ends in a similar way as indicated above with respect of the desired "Kieler Knochenspan". The advantage of the latter is that the synthetic apatite ceramic does not contain immunogenic albumin component. On the other hand there exits a disadvantage in that the synthetic apatite ceramic does not closely imitate natural bone structure, more particularly in the combination of corticalis and spongiosa as in the case of the "Kieler Knochenspan" as does natural bone tissue. In order to achieve similar solidity a greater density with smaller porousness is required which in the case of "Kieler Knochenspan" hinders the subsequent development by the growth of the healing tissue and the natural regenerative bone formation.

In order to avoid the barrierlike obstacles which are bounded to the use of bone substitute material on natural base or spongy apatite ceramic, it is now proposed to achieve a bone induction by means of a mixture of synthetic apatite and cleaned collagen fleece whereby the cleaned immunogen free collagen acts principally as distributing support (see EP-A-0 030 583). This bone substitute material shows very good bone regeneration which leads rapidly to the building of a natural spongy bone network and is well adapted to fill up bone cavities and also as position plastics on still existing endogenic bones, for example in the case of fractures, pseudoarthrosis or stiffening operations of the spinal column. However the material is less well adapted to bridge free defect sections as for example those appearing by defect pseudoarthrosis or cross sectional resections of the bone in the case of bone tumors.

With respect to the prior art there exists therefore a need for a form stable bone substitute material for acting as a matrix for bone regeneration, which, in opposition to the known "Kieler Knochenspan" is absolutely free of antigen that is entirely free of organic substances, which corresponds as far as possible to the natural bone structures and which is similar or identical to the natural human bone. Such a material would permit natural regeneration of bone parts or entire bones destroyed by diseases and removed by surgical procedure. Although the preceding described apatite ceramic may achieve bonelike structures, it is still not possible to produce with it genuine natural bone structures provided through a dense, stable cortex with the corresponding small vascular channels (small channels of Volkmann) and natural spongiosa structures and which promote the growth of healing tissue and the regeneration and which show an optimal biological architectonics.

This leads to the problem of submitting natural bone tissue to a total dealbumination and to liberate it also of the collagen substances which still remain in the bony frame work in the manufacturing process according to DE-A-961 654 for the known "Kieler Knochenspan" so that finally there remains only the natural mineral substance in form of the natural bony frame work. Only a clean "mineral bone" with full dealbumination is reliably free of antigen and it cannot release disturbing immunological rejection reactions after implantation. Such a material would also be superior to the synthetic apatite ceramic because the latter "mineral bone" which is derived from natural bone tissue is not a more or less successful imitation in its chemical mineral composition, mineral crystallization and structure arrangement but it corresponds fully to the natural mineral bone structure.

Attempts to realize full dealbumination with chemical maceration procedures have not been successful. Either full dealbumination and therewith immunological liberty could not be achieved or the known processes have produced, for example through additional boiling, a swelling of the collagen fibers with explosion of the internal mineral structure so that the bone splints have lost the mechanical cohesion and crumbled.

Early and repeated attempts has been made to burn and glow out bone material since the year 1895. Nevertheless, these procedures have not led to successful results because it has been found that glowing often carbonize the soft parts and obstructs the small channels of the bones which produces a chemical and mechanical resistance to the penetrating parts of tissue after transplantation. Bones previously boiled in bicarbonat solutions lose their internal cohesion and crumple. Prior glowing of bone pieces took place on a grate using a Bunsen flame for a maximum of 2 hours. Bauermeister, one of the inventors mentioned in the above German patent came to the conclusion that this process has a theoretical but no practical meaning because the resulting splint has no mechanical strength.

SUMMARY OF THE INVENTION

An object of the present invention is to realize a bone substitute material on a base of natural bone which is entirely free of antigen and which exhibits a sufficient solidity for serving as a form stable matrix for bone regeneration and also for bridging free defect sections. Another object of the invention is to simplify and speed up the manufacturing process of bone substitute material. Bone substitute material on a base of natural bone according to the invention is characterized in that it is completely free of albumin and antigen through premaceration, pyrolization and sintering and in that its frame work consists of only the natural mineral structure of the bone. The process for manufacturing the bone substitute material according to the invention comprises the steps of submitting the bone pieces to a pretreatment for removing the soft parts then to dealbumination by means of a solution of at least 10% $H_2O_2$ or a solution of trypsin and then to degreasing by means of ether. These treated bone pieces are then submitted to combustion in a stove heated to between 400° C. and 1500° C. under air supply and then to sintering.

DESCRIPTION OF THE PREFERRED EMBODIMENT

The invention will be described further by means of examples.

With respect to the following described process bone tissue of human, or other animal origin, more particularly from young pigs and calves, is first subjected to a careful partial maceration in the chemical or enzymatical manner and then to a careful combustion of the inorganic substances with subsequent glow sintering of the remaining mineral substances.

In the case of the whole pretreatment and maceration one has to take care to avoid as far as possible any explosive effect caused for example by freezing or boiling of the natural frame structures of the bone. Consequently, the fresh human bone material from the operating theatre or the animal bone from the slaughterhouse are generally processed in fresh condition, in all cases at short term at temperatures slightly above the freezing point.

Further treatment takes place in the first step of the process after the bone material has been heated to about 40° to 50° in order to maintain the fatty tissue in the bone tissue liquid in order to facilitate rinsing. For this purpose the bones may be heated to this temperature for a short time in a water bath.

Next the adhering soft parts of the bone (muscles, periosteum, articular cartilage) are removed and the bone is sawed for example by means of a bone band saw, to take the form and size corresponding to the needs of the operation. Then the marrow tissue and grease as mechanically removed, for example by scraping and subsequently spraying with a strong hot water shower stream, preferably on a sieve. Subsequently, the bone is subjected to a water treatment for washing off any still adhering soft parts. Then decantation, possible repeated spray cleaning, water treatment and careful spin drying at temperatures of about 50° C. In comparison to the process according to DE-A-961 654 which takes 2–3 days the process according to the invention requires only 2–3 hours.

The second step involves the fine maceration in a solution of hydrogen peroxide. For this, the bone material is carefully rinsed in containers with a solution of 10–30% of hydrogen peroxide which can technically take place by introduction of the bones pieces with a basket sieve of rustproof steel or ceramics. When the bone pieces are immersed in the solution of hydrogen peroxide the latter liberates oxygen which leads to the detachment of albumin and fatty tissue from the surface and the small channels of the bones. The removed particles are brought to the surface by the oxygen gas. At the same time the bone tissue experiences disinfection and bleaching. This procedure is repeated if necessary one or two times until the bone tissue appears entirely white clean. Subsequently, decantation and foehn drying of the bone pieces at a temperature (about 50° C.). takes place. Relative to the prior art, gain in time similar to that described above relative to of the first step is associated to this second step.

Subsequently, in the third step, further fine degreasing through immersion of the dried bone pieces in ethyl ether in which the fatty tissue is removed takes place. The ether may be recovered by subsequent distillation. After decantation of the ether and removal of the basket or the like containing the bone pieces, air drying takes place followed by foehn drying at about only 50° C. after extensive evaporation of the ether in order to avoid any risk of explosion. In accordance with the above process the first three steps may be accomplished within about 6 hours in comparison with the 6–8 days required by the process according to DE-A-961 654.

Subsequently, in fourth step of the process, combustion of the remaining collagen substances of the bone frame in a ceramic stove having precise temperature regulation takes place. This subsequent heating takes place under an air supply so that proper combustion of the organic substances and no carbonization occurs. It is essential that the combustion takes place with a slow increase in the stove temperature so that the collagen substance dries further and that no steaming occurs inside the bone thus avoiding explosion of the crystalline structures. The slow increase of the temperature also prevents the combustion gases from producing high pressure within the bone by permitting the gases to carefully dissipate. The temperature is therefore controlled to increase slowly so that it reaches after about a quarter of an hour 400° C., after a half hour 800° C. and finally after a hour about 1000° C. to 1500° C., preferably about 1250° C.

It is essential to recognize that the heating is executed not only for the purpose of full dealbumination but that subsequently a long lasting heating is executed for the purpose of ceramic sintering or vitrifying of the natural mineral structures of the bone tissue. This results in reinforcement by sintering of the material which is very fragile because of the loss of the internal collagen fiber connection resulting from the prior short combustion procedure.

Mechanical investigations have shown that similarly pretreated spongiosa tissue has small solidity after having been submitted to a relatively short glowing up to 2 hours as previously executed and that it may be easily crushed. It is therefore not well appropriated for repairing bone defects. On the other hand, a higher solidity of the bone frame is achieved by a ceramic sintering lasting several hours which is executed after the combustion procedure. However this higher solidity does not reach that of the fresh natural bone tissue which corresponds to a very firm bounding material due to the content of collagen fibers. Nevertheless it is possible by sintering to achieve a solidity which is sufficient for the practical purposes thus sufficiently compensating the loss of solidity caused by the destruction of the collagen fibers.

In accordance with solidity measurements, sintering should preferably be performed at least between 2 and 20 hours at about 1250° C., preferably for 4, 8 or 10 hours.

The bone pieces should not be removed and cooled suddenly from the ceramic stove to avoid the formation of "chilling bridges" with loss of solidity of the sintered bone structure. It is much more favorable to cool down the bones slowly during several hours by decreasing the temperature in the ceramic stove. The cooling process should last preferably up to 24 hours.

The bone tissue is rendered free of germs by the vitrifying process so that it is sterilized. It may then be brought by means of a sterile instrument into a sterile container and forwarded for use.

It is also possible to package the cooled bone material in radiation permeable plastic containers and to submit it to an additional sterilization procedure by radiation.

The bone material in the course of the sintering procedure has a tendency to shrink which not only affects the dimensions of the bone pieces but also causes the wall lattice work of the spongy bone material, which according to SCHWEIBERGER offers a resistance to the growth of the healing tissue and to the subsequent reshaping of the bone tissue, to contract to more cord-like small bone beams. The bone frame work produced in this way therefore exhibits a relative enlargment of the meshes as compared to these small beams which is favorable for development; that is for growth, in the bone frame work, of healing tissue and reshaping of newly formed living bone. The volume shrinkage of the remaining mineral substance does not cause a weakening but instead a mechanical reinforcement because of the compression. There is thus produced a double favorable effect.

Further investigations with the electron-scan microscope of the bone material produced in this way show that the crystalline arrangement of the bone tissue is preserved by the careful procedure.

The hydroxylapatite which is preponderant in the natural bone mineral is also chemically preserved. This is shown by roentgencrystallographic examinations which show an unaltered pronounced apatite structure.

After introduction in distilled water of the bone produced in this way, a light alkaline reaction is produced which supposes that by the sintering procedure some calcium oxide is liberated which, after being introduced in watery solutions as calcium hydroxide, produces a slight alkaline pH-variation. The latter is also favorable because from experience it is known that the new formation of bone requires a slightly alkaline medium. Also a few light soluble low calcium phosphates are possibly produced which from experience are known to chemically stimulate bone tissue with regard to the formation of bone.

Microradiographical and histological investigations show that after implantation of bone material produced in accordance with the invention, into defect cavities in the growing healing tissue (granulation tissue), there are no foreign body reactions and the healing tissue is rapidly stimulated to formation of new bone. The latter occurs by separation of cancellous bone through bone forming cells (osteoblast) immediately on the small beams of the implanted bone material as well as on the meshwork of the narrow space. Due to the fact that the organization process is not disturbed by foreign body reactions, the reconstruction of natural bone and marrow structures is accelerated so that the marrow spaces are in part already filled with blood forming marrow after a few weeks.

The bone material produced in this way is not only useful for refilling bone defect cavities or for deposit on surfaces, but more particularly also for bridging of greater bone defects for which stability of the form and ability to support a light mechanical load are required. It serves as a matrix for natural bone reconstruction which is self stimulated by the material of implantation. Due to the fact that it is sintered to assume the form of thin small beams, the newly formed bone tissue may better spread out in the marrow spaces at the surface and can take over more rapidly the functional loading as in the case of only partially macerated bone splints with relative bulky bone shelves.

The material can also be used in grinded form also for bioactivation of bone cement, plastics anchoring parts or articular endoprosthesis or other bone substitute materials.

The bone regeneration effect may be reinforced by inoculation of autologous bone marrow extract. It is also possible to provide a preoperative loading with fibrin or dissolved collagen as well as with various antibiotics in form of powder or by immersion in a solution of antibiotics.

It appears essential that by the full replacement of human bones on the base of human bones (from preparations of amputations or dead body) the possibility exists to provide the articular surfaces with articular prosthesis, for example at the hip-joint by mounting (cementation) an articular surface substitute, respectively a partial or total hip prosthesis.

In order to facilitate the growth of entire bones the latter should be provided preferably already before the production procedure with a plurality of drill holes of about 3 mm in diameter and with a raster distance of about 1 cm in order to facilitate the growth of the healing tissue (granulation tissue).

The possibility also exists, for increasing the stability, to provide the bone with a centromedullar pegging or to screw on a stabilizing rail at the surface (osteosynthesis plate).

The implant may be submitted to an increased loading only after sufficient natural bone regeneration has taken place.

Together with the form of determined bones or bone parts, the bone material material may also exists in form of chips, slices, cubes or similar.

We claim:

1. A process for producing a shapable bone substitute material capable of bioactivation from a base of natural bone, comprising the steps of:

removing any soft parts adhering to the natural bone;
removing albumin from the natural bone by immersion in a solution consisting of one of the group of 10% $H_2O_2$ and trysin essentially without the use of caustic material;
degreasing the natural bone by means of ether;
heating the natural bone in accordance with a slowly increasing, controlled temperature profile to a temperature in the range of from about 400° C. to 1500° C. under a supply of air to combust any remaining collagen substances without damaging the mineral structure of the bone;
sintering the natural bone to vitrify its mineral structure and form the bone substitute material; and
slowly cooling the resulting material.

2. The process according to claim 1 wherein the step of slowly cooling comprises cooling for on the order of 24 hours to prevent stresses, cracks or brittleness.

3. The process according to claim 1 wherein the step of heating further comprises:
heating the natural bone to a temperature of about 400° C. over a time period of about fifteen minutes and subsequently heating the natural bone to a temperature of about 800° C. over the following about fifteen minute time period and subsequently heating the natural bone to a temperature of between about 800° C. and 1500° C.; and
wherein the step of sintering further comprises sintering the natural bone for a period of at least about two hours.

4. The process according to claim 3 wherein the step of heating further comprises heating the bone to a temperature of about 1200°–1300° C. in about one hour and the step of sintering further comprises sintering for about 4 to 18 hours.

5. The process of claim 1 wherein said step of heating further comprises heating to a temperature in the range of from about 1200°–1300° C.

6. The process according to claim 1 wherein the step of removing soft parts further comprises: heating the natural bone in a water bath at a temperature of 40° C. to 50° C.;
mechanically removing the soft parts from the bone;
spraying the bone with a strong water stream; and
spin drying the bone at 50° C.; and
wherein the step of removing albumin further comprises immersing the bone in a solution of 10 to 30% $H_2O_2$ in a shaking machine and drying the bone in a warm air stream.

7. The process according to claim 1 further comprising the step of sterilizing the bone substitute material by subjecting said material to radiation.

8. The process according to claim 1 further comprising the step of introducing at least one of the group comprising fibrin, dissolved collagen and antibiotics in powder or dissolved form to the bone substitute material to reinforce bone regeneration effects.

9. The process of claim 1 further comprising the step of shaping the bone substitute material in the form of a bone part to be replaced.

10. The process of claim 1 further comprising step of forming the bone substitute material in the form of chip.

11. The process of claim 1 further comprising step of forming the bone substitute material in the form of slice.

12. The process of claim 1 further comprising step of forming the bone substitute material in the form of cube.

13. The process according to claim 1 further comprising the step of inoculating the bone substitute material with autologous bone marrow extract.

14. The process according to claim 1 further comprising the step of providing the bone substitute material with holes before the heating and sintering steps.

15. The process of claim 14 wherein the step of providing the bone substitute with holes further comprises drilling holes having a diameter on the order of about 3 mm. and a raster distance of about 10 mm.

16. The process of claim 15 further comprising the step of providing the bone substitute material with an artificial article for increased stability during use.

17. The process of claim 15 further comprising the step of providing the bone substitute material with a marrow space rail.

18. The process of claim 17 further comprising the step of providing the bone substitute material with a centro-medullar pegging.

19. The process of claim 17 further comprising the step of providing the bone substitute material with an osteosynthesis plate.

* * * * *

UNITED STATES PATENT AND TRADEMARK OFFICE
CERTIFICATE OF CORRECTION

PATENT NO. : 4,654,464

DATED : Mar. 31, 1987

INVENTOR(S) : Heinz Mittelmeier; Bernhard Mittelmeier; Beat Leu

It is certified that error appears in the above—identified patent and that said Letters Patent is hereby corrected as shown below:

On the title page, in box "[30]" entitled

"Foreign Application Priority Data"

the date "Oct. 20, 1984" should be

"Oct. 20, 1983".

Signed and Sealed this

Eighth Day of September, 1987

Attest:

DONALD J. QUIGG

Attesting Officer

Commissioner of Patents and Trademarks